United States Patent
Zinger

(12)
(10) Patent No.: US 6,357,489 B1
(45) Date of Patent: Mar. 19, 2002

(54) DEVICE FOR STORING A LIQUID MEDICINAL SUBSTANCE AND METHOD FOR FILLING AN APPLICATOR FOR A LIQUID MEDICINAL SUBSTANCE BY USE OF SAID STORING DEVICE

(75) Inventor: Freddy Zinger, Raanana (IL)

(73) Assignee: Omrix Biopharmaceuticals S.A. (BE)

( * ) Notice: Subject to any disclaimer, the term of this patent is extended or adjusted under 35 U.S.C. 154(b) by 0 days.

(21) Appl. No.: 09/601,614

(22) PCT Filed: Feb. 4, 1999

(86) PCT No.: PCT/EP99/00743

§ 371 Date: Sep. 27, 2000

§ 102(e) Date: Sep. 27, 2000

(87) PCT Pub. No.: WO99/39642

PCT Pub. Date: Aug. 12, 1999

(30) Foreign Application Priority Data

Feb. 4, 1998 (DE) .......................... 198 04 224

(51) Int. Cl.$^7$ ................................. B65B 1/04
(52) U.S. Cl. ................. 141/2; 141/18; 141/98; 141/329; 141/27; 604/415
(58) Field of Search .................... 141/2, 18, 21–27, 141/98, 329, 330; 604/403–415

(56) References Cited

U.S. PATENT DOCUMENTS

| | | | |
|---|---|---|---|
| 4,874,368 A | | 10/1989 | Miller et al. |
| 4,978,336 A | | 12/1990 | Capozzi et al. |
| 5,354,287 A | * | 10/1994 | Wacks .......................... 604/232 |
| 5,494,087 A | * | 2/1996 | Pitelka et al. ................ 141/375 |

FOREIGN PATENT DOCUMENTS

| | | |
|---|---|---|
| DE | 42 23 356 A1 | 7/1992 |
| EP | 0 037 393 | 10/1981 |
| EP | 0 315 222 B1 | 12/1984 |
| EP | 0 210 160 B2 | 1/1987 |
| WO | WO 95/31137 | 11/1995 |
| WO | WO 96/19940 | 7/1996 |

* cited by examiner

*Primary Examiner*—Steven O. Douglas
(74) *Attorney, Agent, or Firm*—Diller, Ramik & Wight

(57) ABSTRACT

The device for storing a liquid medicinal substance, particularly a component of a multi-component tissue adhesive, comprises a vessel (12) for the medicinal substance, the vessel (12) having a bottom wall (14), a side wall (16) and an opening (22) opposite the bottom wall (14) and closed by a closure body (24) which in turn is pierceable from outside by a puncture needle placed into sealed abutment. The device further comprises a receiver cup (26) for said vessel (12), the receiver cup (26) having a bottom wall (28) and a side wall (30) formed with an edge (32) delimiting the side wall (30) at its upper end opposite the bottom wall (28).

11 Claims, 5 Drawing Sheets

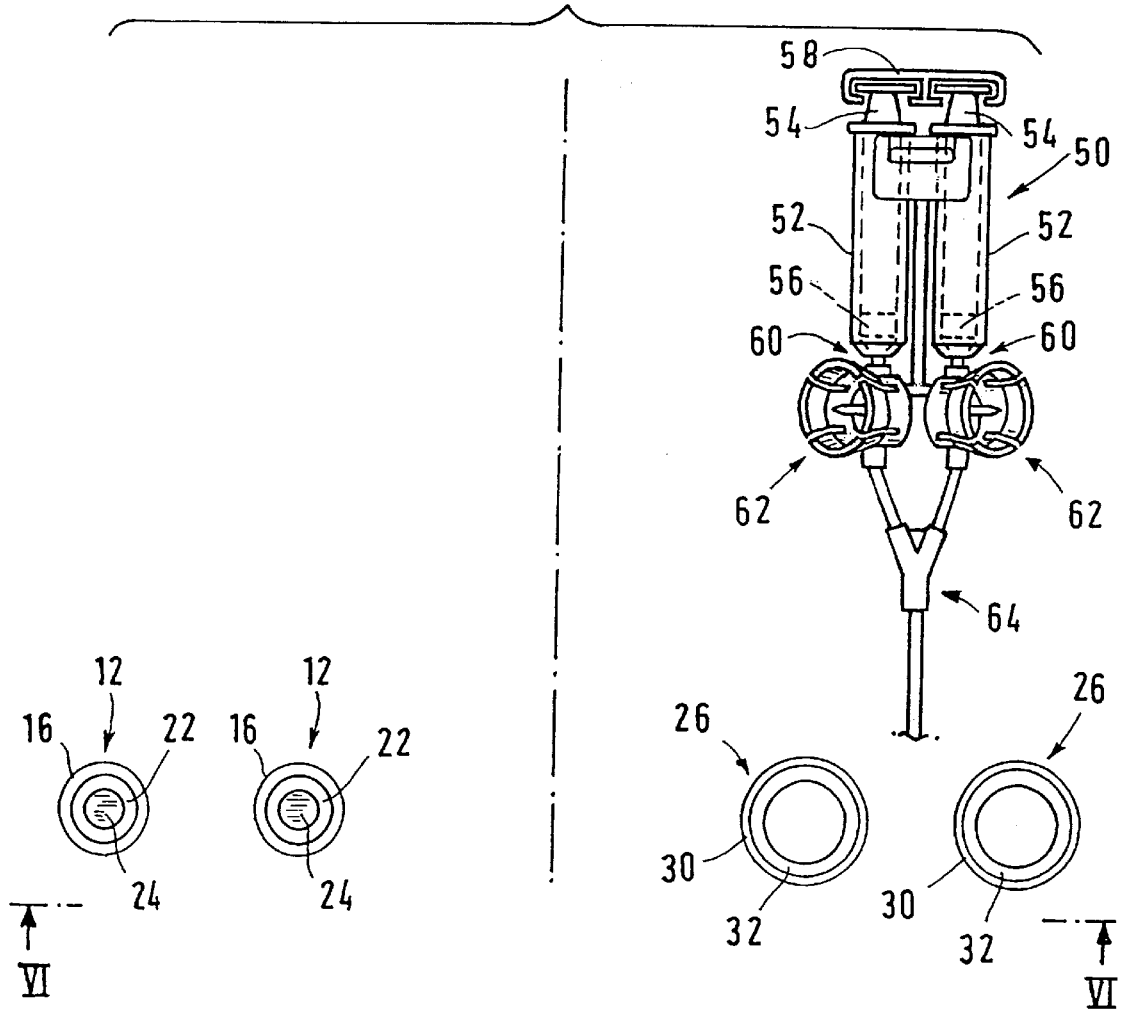
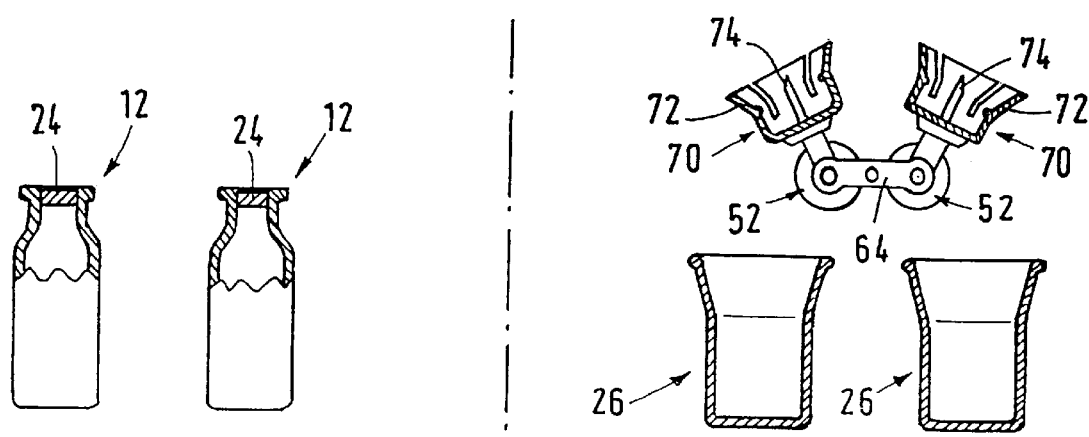

DEVICE FOR STORING A LIQUID MEDICINAL SUBSTANCE AND METHOD FOR FILLING AN APPLICATOR FOR A LIQUID MEDICINAL SUBSTANCE BY USE OF SAID STORING DEVICE

BACKGROUND OF THE INVENTION

The invention relates to a device for storing a liquid medicinal substance, particularly a substance forming a component of a multi-component tissue adhesive. The invention further relates to a method for filling an applicator for a medicinal multi-component substance, particularly for a multi-component tissue adhesive, with the individual components of the medicinal substance and the tissue adhesive, respectively, by use of the above mentioned device.

Known from EP-B-0 037 393, EP-B-0 210 160, U.S. Pat. No. 4,874,368, U.S. Pat. No. 4,978,336, DE-A-42 23 356, EP-B-0 315 222, WO-A-96/19940 and WO-A-95/31137 are applicators and respectively application devices provided for two-component tissue adhesives and comprising two substantially syringe-body-shaped supply containers attached to the connecting ends of a dispenser device which in turn comprises a dispensing end for dispensing the individual components. The preparation of such an applicator for use e.g. in an operating theater is relatively bothersome and requires a certain routinized skill. For instance, each component of the tissue adhesive has to be introduced in the individual supply containers. The individual components are usually delivered in ampoule-shaped glass vessels having their openings closed by a closure body (septum or the like). By means of a puncture needle mounted to the distal end of the supply container, the closure body is perforated for subsequent suction of its the contents into the supply container. Then, the supply container has to be separated from the puncture needle and connected to the dispenser device. Thus, the preparation of the applicator necessitates a large number of individual steps which are made still more aggravating since the person holding the applicator during filling will have to work under sterile conditions whereas the vessels for the individual components are usually not sterile and thus should not be held by this person. For this reason, these vessels are held by a second person who will position the vessels in such a manner that the person holding the applicator can pierce the puncture needles into the closures bodies for filling the supply containers. In this regard, the risk of injuries to the person holding the vessel should not be underestimated.

The state of the art further includes three-way valves comprising three connectors provided with a switching element for switching the fluid connection. In this case, the switching element is arranged for movement between a first position wherein the first connector is in fluid connection with the second connector and the third connector is shut, and a second position wherein the first connector is in fluid connection with the third connector while the second connector is shut. A three-way valve designed especially for the use of receiving vessels for medicinal substances and having its opening provided with a pierceable closure body is known from WO-A-96/29113.

It has already been proposed to connect the three-way valve known from WO-A-96/29113 between the supply containers and the dispenser device of an applicator for multi-component adhesives. On the one hand, the resultant applicator arrangement is filled in a considerably easier manner because the mechanical connection between the dispenser device and the supply containers is not cut off during the filling process; thus, already before the filling and up to the switching of the three-way valves, the connector will be in the same condition which it will assume also for applying the tissue adhesive. Still, however, the filling process performed by the above proposed applicator with three-way valve is problematic due to the risk that the person holding the applicator and thus working under sterile conditions might come into contact with the outer surface of the vessel which is not germ-free, i.e. is non-sterile.

SUMMARY OF THE INVENTION

It is an object of the invention to provide a device suited to store liquid medicinal substances in such a manner that said substances, in spite of a non-sterile condition of the outer surface of the vessel accommodating the substance, can be handled by a person working under sterile conditions.

To achieve the above object, the invention proposes a device for storing a liquid medicinal substance, particularly a component of a multi-component tissue adhesive, comprising a vessel for the medicinal substance, said vessel having a bottom wall, a side wall and an opening opposite the bottom wall and closed by a closure body which in turn is pierceable from outside by a puncture needle placed into sealed abutment, and a receiver cup for said vessel, said receiver cup having a bottom wall and a side wall formed with an edge delimiting the side wall at its upper end opposite the bottom wall.

The device according to the invention serves for taking up a vessel provided to accommodate a liquid medicinal substance and formed with an opening closed by a closure body pierceable by a puncture needle. According to the invention, a vessel of the above type, whose external surface is not germ-free and which—since its contents would react sensitively to treatment processes for sterilizing its outer surface—should not be sterilized after filling, can be accommodated in a receiver cup which in turn can be sterilized by the known method. The combination of vessel and receiver cup resulting from the above arrangement can now be handled also by a person working under sterile conditions.

The inventive measure of inserting a vessel with a non-sterile outer surface into a sterilized receiver cup, is suited to facilitate—under the aspect of the safeguarding of a germ-free working process —especially the filling of an applicator for a medicinal multi-component substance and particularly for a multi-component tissue adhesive if the applicator comprises three-way valves adapted to have the vessels coupled thereto and arranged between the supply containers and the dispenser device of the applicator. By means of the inventive device, the filling process will now be performed in that the person working under sterile conditions holds the receiver cup while keeping the opening thereof unobstructed so that another person can introduce the vessel containing the medicinal substance, with the bottom wall thereof facing towards the bottom wall of the receiver cup, into the receiver cup. All of the subsequent processing steps during the filling of the applicator are then carried out by the person working under sterile conditions, with an extremely low danger of this person coming into contact with non-sterilized surfaces of the vessel. Notably, by the same person who also holds the applicator, the vessel arranged in the receiver cup held by that very person can also be mounted onto the coupling adapter of the three-way valve so that, thereafter, the medicinal substance can be sucked from the vessel into the respective supply container by displacing the pistons of the supply containers. By moving the fluid switching element of the three-way valve, the applicator can now be directly used for application, if desired, after removal of the receiver cup holding the vessel therein.

For the handling of the applicator during filling, it is of advantage if the three-way valves comprise the features described in WO-A-96/29113. Thus, particularly, it may be suitably provided that the fluid connection of the three-way valve can be changed by a simple rotating movement of the fluid switch element. Further, it may be suitably provided that the coupling adapter designed to receive the opening region of the vessel is supported for rotation and is connected to the fluid switch element for rotating the latter along with the rotation of the adapter. Further, it is useful for the handling of the applicator during application if the applicator, after the fluid switch element has been moved into its position for establishing a fluid connection between the supply container and the dispenser device of the applicator, can be easily detached.

For the handling of the receiver cup together with the vessel received therein, the hold of the vessel in the receiver cup should be effected in a manner securing the vessel against undesirably falling out of the cup. This can be realized by a retaining means, particularly a retaining means generating friction. By way of alternative, the receiver cup can be formed in such a manner or from such a material that, by application of a force on two sites substantially diametrically opposed to each other, the receiver cup can be elastically deformed, thus obtaining a clamping hold of the vessel in the receiver cup by the force externally applied to the latter.

A device generating friction between the side walls of the vessel an the receiver cup can be realized particularly in that the side wall of the receiver cup is provided with inwardly projecting elastic tongues which preferably are integrally formed to the side wall. Normally, the receiver cup will be made of plastic so that the above spring tongues can be produced by a corresponding configuration of the injection-molding tool provided for the production of the receiver cup. To make it possible that the elastic tongues will have enough freedom for upward movement during insertion of the vessel although the outer diameter of the receiver cup is only slightly larger than that of the vessel, it can be of advantage to provide the side wall of the receiver cup with openings in alignment with the elastic tongues.

Advantageously, each elastic tongue is provided with a first portion connected to the side wall and extending at an inclination thereto, which first portion is joined by a second portion arranged substantially along the extension of the side wall of the receiver cup and preferably ending in the immediate vicinity of the bottom wall. As has been proven in practice, three elastic tongues arranged at a mutual displacement of 120° will be sufficient for generating the required friction by which the vessel, e.g. made of glass, is secured in the receiver cup.

Regarding the configuration of the receiver cup provided with said retaining means for securing the vessel in the receiver cup against undesirably sliding out, it is an essential aspect that the receiver cup, in spite of the retaining means, is made from just one material. Exactly this additional requirement is met when the retaining means is realized by the above described elastic tongues, since these elastic tongues are made from the same material as that of the receiver cup and particularly can be generated along with the receiver cup in the same production process (plastic injection-molding technique).

An embodiment of the invention and particularly the process for filling an applicator for medicinal substances will be explained in greater detail hereunder with reference to the Figures. In the Figures:

BRIEF DESCRIPTION OF THE DRAWINGS

FIGS. 5 to 12 are views illustrating the individual procedural steps and conditions of the applicator while its supply containers are being filled with the medicinal substances.

DESCRIPTION OF THE PREFERRED EMBODIMENTS

Figure 1:
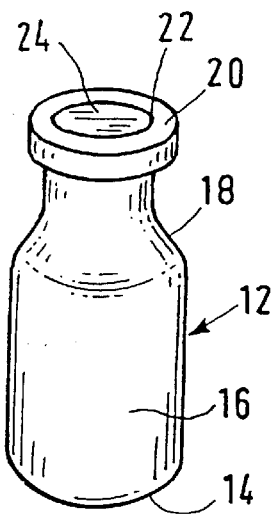
FIG. 1 is a perspective view of a usual glass vessel in ampoule form for a medicinal substance, comprising a closure body to be pierced by a hollow needle.

With reference to FIGS. 1 through 4, the receiving means 10 according to a first embodiment will be described hereunder. Receiving means 10 comprises a vessel 12 for the medicinal substance which can be particularly a component of a tissue adhesive. Vessel 12 is provided as a glass ampoule and comprises a bottom wall 14 and a side wall 16. Towards the upper end facing away from bottom wall 14, vessel 12 tapers in the manner of a bottleneck and is formed with a shoulder 18 joined by a bead 20 delimiting an opening 22. Arranged in opening 22 is a plastic closure body 24 adapted to be perforated by a hollow needle; the closures body 24, when perforated by the hollow needle, is sealed relative to the needle in an air-tight manner.

Figure 2:
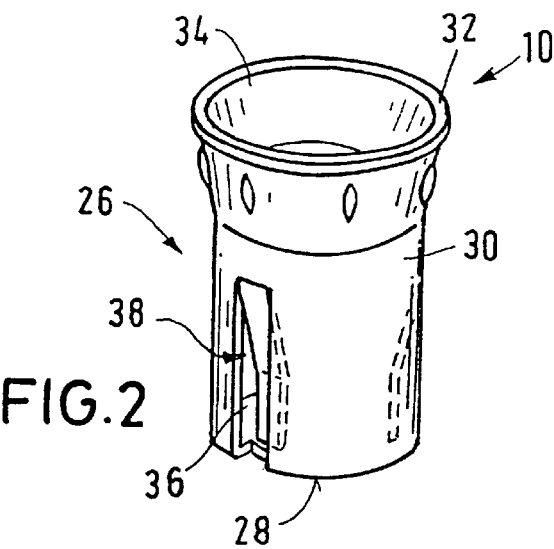
FIG. 2 is a perspective view of a sterilizable plastic receiver cup for the glass vessel according to FIG. 1.
Figure 3:
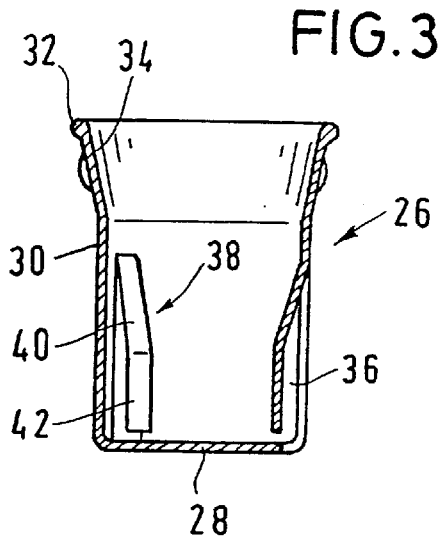
FIG. 3 is a longitudinal sectional view of the receiver cup according to FIG. 2 without the glass vessel arranged therein.

The above glass vessel 12 is configured for insertion into a plastic receiver cup 26 which in FIGS. 2 and 3 is shown in a perspective and a longitudinal sectional view, respectively. Receiver cup 26 comprises a bottom wall 28 and a surrounding side wall 30 which on its upper end, facing away from bottom wall 28, is slightly conically flared, and which has an upper edge 32 delimiting a receiving opening 34. The side wall 30 of the receiver cup is formed with three recesses 36 extending down into bottom wall 28. Arranged in alignment with these recesses 36 and inward of side wall 30, three elastic tongues 38 are formed integrally with the side wall 30 of receiver cup 26. The elastic tongues 38 comprise a first portion 40 connected to side wall 30. This first portion 40 is joined by a respective second portion 42 arranged at an angle relative to first portion 40 and oriented substantially in parallel to the extension of side wall 30. This second portion 42 ends immediately above the bottom wall 28 of receiver cup 26.

Figure 4:
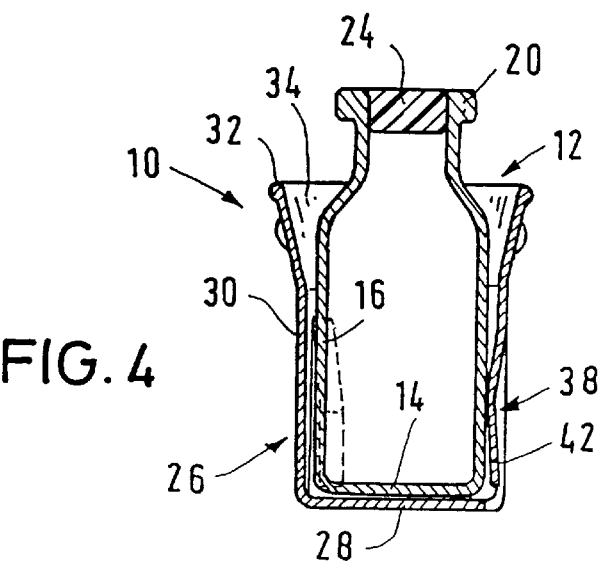
FIG. 4 is a longitudinal sectional view of the plastic receiver cup according to FIG. 3 with the glass vessel arranged therein.
Figure 7:
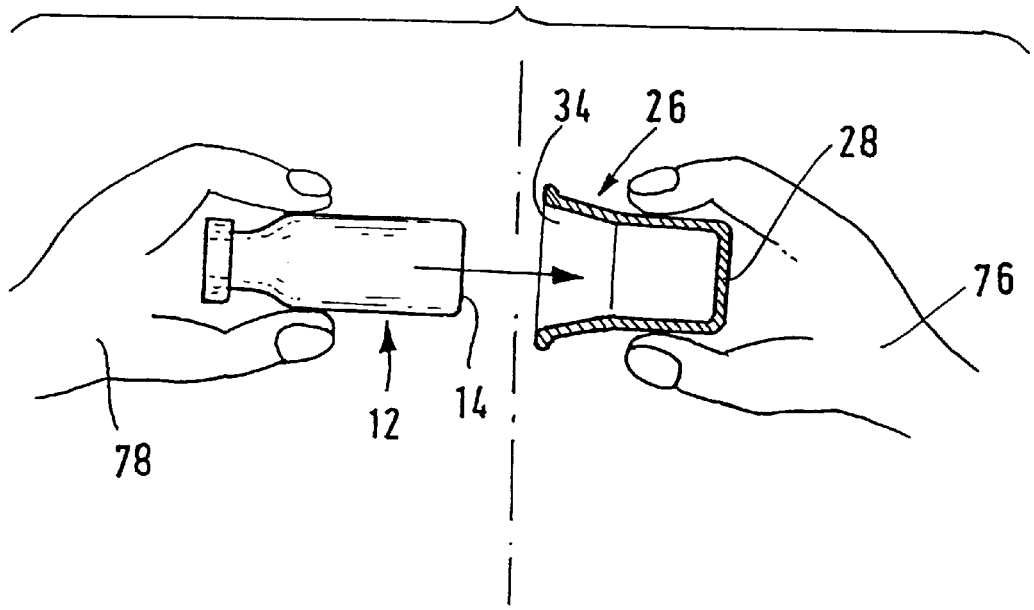
Figure 8:
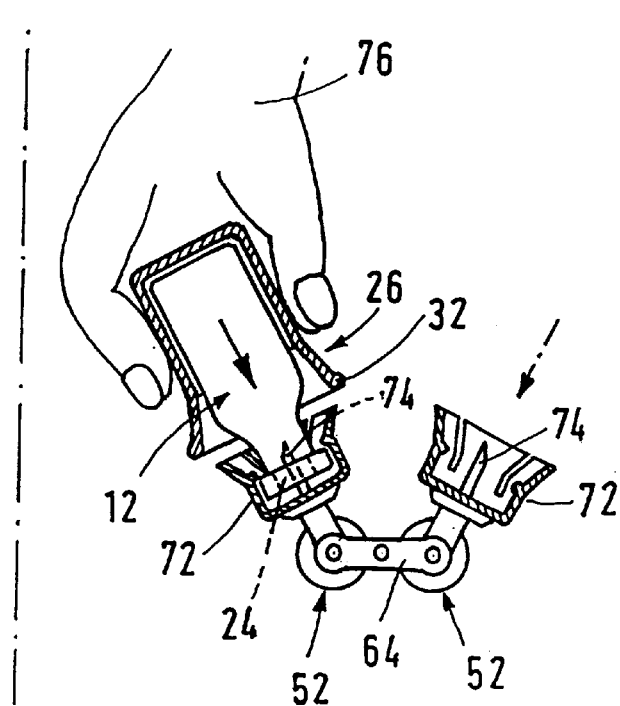
Figure 9:
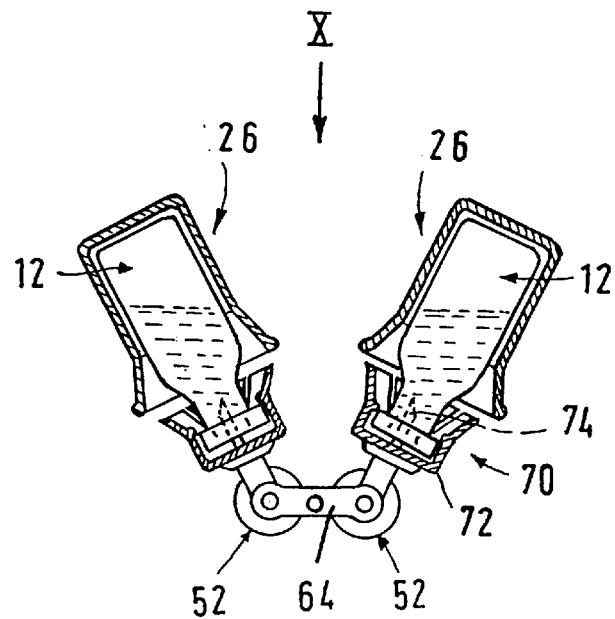
Figure 10:
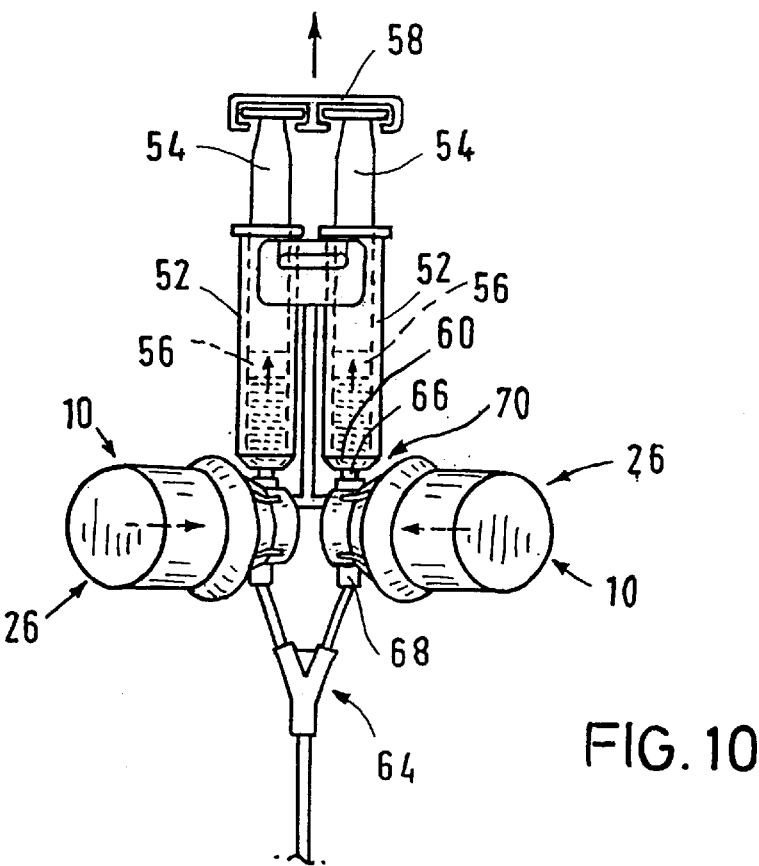
Figure 11:
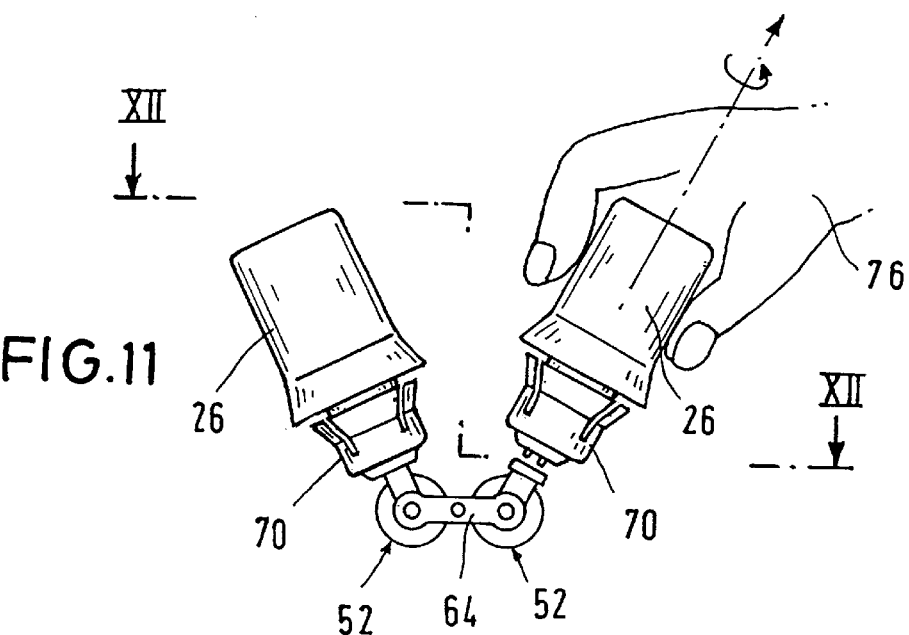
Figure 12:
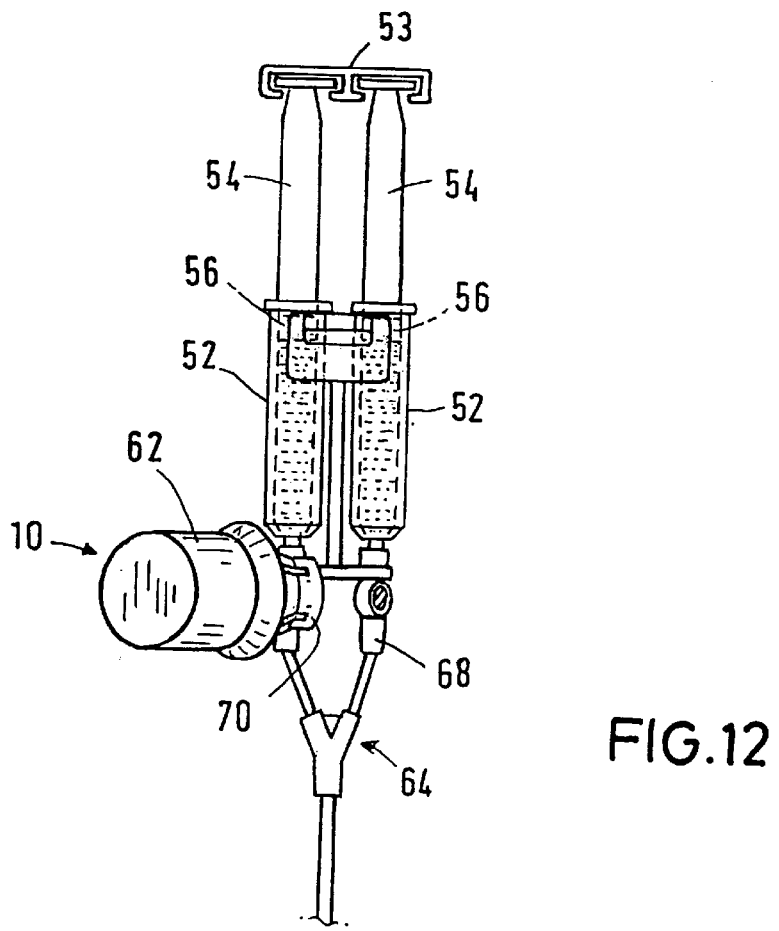

In the inserted condition of glass vessel 12 in receiver cup 26, the three elastic tongues 38 are elastically deformed by being moved towards the outside. In this condition, the second portions 42 of the tongues are situated in the recesses 36 of side wall 30. This situation is illustrated in FIG. 4.

Using the receiving means 10 according to FIGS. 1 to 4, e.g. a tissue adhesive applicator 50 for application of a multi-component tissue adhesive can be filled in a simple manner. The applicator 50 and the filling process will be explained hereunder with reference to FIGS. 5 to 12.

The applicator 50 comprises two supply containers 52 formed in the manner of syringe bodies and having pistons 56, held by piston rods 54, arranged therein for sliding displacement. The piston rods 54 are arranged to project from the rear ends of the syringe bodies 52 and are coupled to each other by an attachable connection member 58. The front ends 60 of each supply container 52 are connected to three-way valves 62 which in turn are connected to a dispenser device 64 for dispensing the tissue-adhesive components accommodated in the supply containers 52. Each three-way valve comprises a first connector piece 66 connected to the front end 60 of a supply container 52 and a second connector piece 68 connected to the dispenser device 64, as well as a third connector piece 70 (see especially FIG. 10). The third connector piece 70 is provided with a coupling adapter cap 72 for receiving the tapered upper end of a glass vessel 12 and is provided with a puncture needle 74 arranged to penetrate the closure cap of the vessel 12 when the vessel 12 is inserted into adapter cap 72 (see especially FIG. 9). For reasons of a clearer illustration of the handling of the applicator during the filling process using the receiving means 10, the movable switching elements in the three-way valves 62 are not shown. These switching elements are coupled to the adapter caps 72 and can be moved by the latter between a first position and a second position. In the first position, a fluid connection exists between the first connector piece 66 and the third connector piece 70 of a three-way valve 62, while in the second position the first connector piece 66 is in fluid connection with the second connector piece 68. The three-way valves 62 are further configured to allow removal of the adapter caps 72 from the rest of the three-way valve 62 when the valves have been actuated to move the switching elements into their second positions.

The process of filling the applicator 10 will be briefly explained hereunder with reference to FIGS. 5 to 12. In this context, the left halves of FIGS. 5 to 12 illustrate the situation on the side of the person working under sterile conditions while the left halves relate to the person not working under sterile conditions. The person working under sterile conditions, using his or her hand 76, seizes a receiver cup 26 and orients the same such that the receiving opening 34 is facing toward the person not working in a sterile environment. This person in turn, using his or her hand 78, will seize a glass vessel 12 and insert the same into the receiver cup 26, with the bottom wall 14 of the vessel facing toward the opening 34 and the bottom wall 28 of receiver cup 26 (see FIG. 7). The outer surface of the closure body 24 of glass vessel 12 is then wiped with a disinfectant (e.g. alcohol) or has already been treated therewith before. Subsequently, the person working under sterile conditions will insert the opening of the vessel 12 arranged in the receiver cup 26 into the adapter cap 72 of the three-way valve 62, with the hollow needle 74 perforating the closure body 24 and entering the interior of glass vessel 12. Since the height of the glass vessel 12 is larger than that of the receiver cup 26, the glass vessel 12 extends beyond the edge 32 of receiver cup 26 when arranged therein (see also FIG. 4).

After the person working under sterile conditions has in this manner mounted the glass vessels 12 along with the receiver cups 26 onto the coupling caps 72 of both three-way valves 26 (see FIGS. 9 and 10), this person, using coupling member 58, will pull both piston rods 54 in rearward direction out of the supply containers 62, thus causing the contents of the glass vessels 12 to enter the supply containers 62 by vacuum force. Subsequently, the person working under sterile conditions seizes the adapter caps 72 by his or her hand 76 to turn the caps so that the switching element is moved from the first position to the second position and the adapter caps 72 can be removed from the rest of the three-way valves (see FIGS. 11 and 12). Then, the applicator 50 is in the condition wherein it has been filled with the adhesive components and is ready for use. During the complete filling process, virtually no danger exists anymore that the person working under sterile conditions might touch the non-sterilized outer surface of the vessels 12 with his or her hands 76. In the above manner, the filling process is considerably simplified and is made considerably safer regarding a danger of disinfection.

Although a preferred embodiment of the invention has been specifically illustrated and described herein, it is to be understood that minor variations may be made in the apparatus without departing from the spirit and scope of the invention, as defined the appended claims.

What is claimed is:

1. A device for storing a component of a multi-component liquid medical substance comprising a vessel (12) for housing a component of a multi-component liquid medical substance; said vessel (12) having a bottom wall (14), a side wall (16) and an opening (22) opposite the bottom wall (14); said opening (22) being closed by a closure body (24) which can be pierced by a puncture needle, a receiver cup (26) for said vessel (12); said receiver cup (26) having a bottom wall (28) and a side wall (30) forming an edge (32) delimiting the side wall (30) at an upper end thereof opposite the receiver cup bottom wall (28); retaining means (38) for securing the vessel (12) in the receiver cup (26) against unintentional sliding outward removal therefrom by generating frictional engagement between the receiver cup (26) and an exterior surface of the vessel side wall (16), and said retaining means (38) including at least one elastic tongue (38) projecting into and at least partially along and being at least partly spaced from an inner surface of said receiver cup side wall (30).

2. The device as defined in claim 1 wherein said elastic tongue (38) projects from the receiver cup side wall (30) and has a free end directed toward the receiver cup bottom wall (28).

3. The device as defined in claim 2 wherein said elastic tongue (38) includes at least a portion thereof in substantially spaced parallel relationship to the receiver cup side wall (30).

4. The device as defined in claim 3 wherein the distance between the vessel bottom wall (14) and the vessel opening (22) is greater than the distance between the receiver cup bottom wall (28) and the receiver cup edge (32).

5. The device as defined in claim 1 wherein said elastic tongue (38) projects into the receiver cup (26) and has a free end spaced from the receiver cup bottom wall (28).

6. The device as defined in claim 5 wherein said elastic tongue (38) includes at least a portion thereof in substantially spaced parallel relationship to the receiver cup side wall (30).

7. The device as defined in claim 1 wherein said elastic tongue (38) includes at least a portion thereof in substantially spaced parallel relationship to the receiver cup side wall (30).

8. The device as defined in claim 1 wherein the elastic tongue (38) is formed from a portion of the receiver cup side wall (30).

9. The device as defined in claim 1 wherein said elastic tongue (38) includes first and second portions (40, 42, respectively), said first portion (40) being connected to the receiver cup side wall (30), and said second portion (42) being disposed substantially parallel to the receiver cup side wall (30) and terminating in a free end.

10. The device as defined in claim 9 wherein the receiver cup (26) includes three elastic tongues (38) arranged substantially equal circumferential distances from each other.

11. A method of filling an applicator with at least one component of a multi-component liquid medial substance comprising the steps of providing an applicator (50) having a plurality of substantially cylindrical supply containers (52) for each housing one component of a multi-component medicinal substance; each supply container (52) having a front end (60) with an outlet opening, a rear end facing away from the front end (60), and a piston (56) slidable in the supply container (52) and having a piston rod (54) projecting from the rear end for actuating the piston (56); a discharge mechanism (64) including connector pieces for fluid connection with the front ends (60) of the supply containers (52) and including a discharge end for discharging a multi-component medicinal substance, at least one fluid connection between the front ends (60) of the supply containers (52) and the connector pieces of the discharge mechanism (64) having a fluid connection switch unit (62); the fluid connection switch unit (62) including a first connector piece (66) connected to the front end (60) of each supply container (52), a second connecter piece (68) connected to one of the supply containers (52) and a third connector piece (70) for fluid connection with the interior of a vessel (12) closed by a piercable closure body (24); the third connector piece (70) including a coupling adapter (72) and a hollow needle (74) for perforating a closure body (24) of a vessel (12); and the fluid connection switch unit (62) having a first position in which the first connector piece (66) is in fluid connection with the third connector piece (70) and the second connector piece (68) is closed, and a second position in which the first connector piece (66) is in fluid connection with the second connector piece (68) and the third connector piece (70) is closed; the method including the steps of:

- holding the applicator (50) by a hand (76) of a first person;
- holding the vessel (12) by a hand (78) of a second person;
- the first person grips a receiver cup (26) at a side wall (30) thereof;
- the second person inserts a vessel (12) into the receiver cup (26) with a bottom wall (14) of the vessel (12) facing the bottom wall (28) of the receiver cup (26);
- the first person assembles the vessel (12) together with the receiver cup (26) onto the coupling adapter (72) of the fluid connection switch unit (62) such that the hollow needle (74) pierces the closure body (24) in the opening (22) of the vessel (12) and penetrates into the interior of the vessel (12), the second person withdraws the piston rod (54) of the supply container (52) connected to the fluid connection switch unit (62) from the rear end of the supply container to cause the component of the medical substance to be sucked from the vessel (12) into the supply container (52) by vacuum; and
- the second person moves the fluid connection switch from the first position to the second position.

\* \* \* \* \*